United States Patent [19]
Hazard et al.

[11] Patent Number: 5,797,855
[45] Date of Patent: Aug. 25, 1998

[54] URINE SPECIMEN AND OTHER BODY FLUIDS COLLECTION DEVICE

[76] Inventors: James Taylor Hazard, 347 Kenwood Way, Louisville, Ky. 40215; R. Vincent Kidd, III, 2101 Robin Ave., Hammond, La. 70403

[21] Appl. No.: 814,652

[22] Filed: Mar. 10, 1997

Related U.S. Application Data

[60] Division of Ser. No. 322,112, Oct. 21, 1994, which is a continuation-in-part of Ser. No. 149,549, Nov. 9, 1993, abandoned.

[51] Int. Cl.$^6$ ............................................. A61B 5/00
[52] U.S. Cl. ..................... 600/513; 600/584; 604/318; 604/331; 604/349
[58] Field of Search ........................... 600/573, 574; 604/329, 318, 321, 324, 327, 346, 349, 347, 353

[56] References Cited

U.S. PATENT DOCUMENTS

| | | |
|---|---|---|
| 2,783,909 | 3/1957 | Roberts . |
| 2,803,370 | 8/1957 | Lennard . |
| 3,335,714 | 8/1967 | Giesy . |
| 4,121,306 | 10/1978 | Bringman et al. . |
| 4,492,258 | 1/1985 | Lichtenstein et al. . |
| 4,895,167 | 1/1990 | Guala . |
| 5,251,639 | 10/1993 | Rentsch . |

*Primary Examiner*—Max Hindenburg
*Assistant Examiner*—Pamela L. Wingood
*Attorney, Agent, or Firm*—Middleton & Reutlinger; Charles G. Lamb

[57] ABSTRACT

A device for collecting uncontaminated liquid specimens, particularly, urine specimens from adult females, adult males and pediatric males. The device includes an elongated flexible tubular conduit member having a funnel-shaped opening at one end to be in sealing relationship with a urethra or glans penis and a discharge end to be received within a sample container. The sample container includes an opening with a sealing member therein to receive the discharge end of the elongated flexible tubular conduit member in an open position for receiving a urine specimen therein and in a closed position when the discharge end of the elongated flexible tubular conduit member is withdrawn.

17 Claims, 4 Drawing Sheets

URINE SPECIMEN AND OTHER BODY FLUIDS COLLECTION DEVICE

CROSS REFERENCE TO RELATED APPLICATIONS

This application is a divisional application of U.S. Ser. No. 08/322,112 filed on Oct. 21, 1994 which is a continuation-in-part application of U.S. Ser. No. 08/149,549 filed on Nov. 9, 1993, now abandoned.

BACKGROUND OF THE INVENTION a) Field of the Invention

This invention relates to the collection of urine specimens and other body fluids from patient groups including adult females, adult males, and pediatric males.

b) Discussion of the Prior Art

Medical science has proven the need for routine urinalyses to detect enumerable disease processes. The most commonly used method for this in the hospital, office practice, home health practice and nursing homes, is a clean catch mid-stream urinalysis. The clean catch mid-stream urinalysis is currently collected in one of many different size cups or containers. However, it has been found that adult females, adult uncircumcised males, and pediatric males have specific and distinct problems in relation to the presently used collection methods. For example, in the adult female, vaginal voiding and contamination by the labia and hair of the vaginal region during the act of micturition renders many of the urinalyses unusable in relation to accurate bacterial red blood cell, leucocyte, and nitrite quantifications. In present practice in order to circumvent this potential contamination the insertion of a tube into the bladder is needed for an accurate urinalysis when looking for an infection. In the adult uncircumcised male, for example, often this person is not instructed in the proper collection of the specimen (pulling the foreskin back and cleansing the glans penis) and therefore contamination occurs when he urinates through the foreskin into the collection device. Also, for example, in the neonatal and young pediatric male, collection devices are generally a bag-like device placed around the scrotum, penis, and suprapubic region, which severely enhances bacterial contamination. Even further, in cases where a patient needs catheterization because a fluid specimen is inaccurate, it has been found that catheterization leads to infection in twenty percent of the patients who are catheterized. Thus, the need for a device for fluid sampling other than catheterized specimens is needed. Additionally the cup containers frequently are spilled in transit to the lab when caps are not screwed on containers properly. This requires recollection of specimens and is very time consuming and cost inefficient.

Moreover, medical science has proved the need for collection of sputum samples for analysis in relation to infections and detection of cancers and viruses as well as for drug testing. In the use of cup containers, the caps for the cups become unscrewed or the caps are not placed correctly on the cups and the specimens spill out. This necessitates re-collection of the specimen which is time consuming and expensive for the patients and the hospitals.

Furthermore, medical science has proven the need for collection of semen analyses for evaluation of patients with infertility and to assess post vasectomy patients. Presently, patients collect specimens for these analyses in baggies, condoms, jars, and cups which have proved to be difficult for physicians and lab personnel to work with.

There have been a number of suggestions for apparatuses for taking urinary samples in the prior art, but none have found acceptability in the medical profession involved with overseeing the taking of samples and transporting said samples for analytical evaluation. One particular reference noted is U.S. Pat. No. Re26,854 which teaches an apparatus for collecting urine samples from female patients which includes a container with an elongated tube sealingly mounted in the open end of the container. The elongated tube on its distal end includes a compressible and resilient pad portion which is adapted to be positioned around the urethral meatus and in use the urine is collected in the sample collector.

SUMMARY OF THE INVENTION

Accordingly, it is a principal object of the present invention to provide an apparatus for improving the collection of urine samples from adult females, adult uncircumcised males, and pediatric males and subsequently decreasing contamination of the samples.

It is another object of the present invention to provide an apparatus for the collection of urine samples which reduces the number of contaminated urine samples obtained from adult females, adult uncircumcised males and pediatric males and subsequently decreasing contamination of the samples.

It is even another object of the present invention to provide an apparatus for the collection of urine specimens to reduce the number of patients being treated unnecessarily for urinary tract infections due to contaminated urine specimens.

It is an even further object of the present invention to provide an apparatus for the collection of urine specimens and reduce the time spent in the transfer of the urine from the collection device to a centrifuge tube by lab or office personnel.

It is an even further object of the present invention to provide a collection device of urine specimens which reduces certain unnecessary health care expenditures due to the re-running of urinalyses due to contamination in obtaining the samples.

Another even further object of the present invention is to provide a urine specimen collection device which includes means to form a tight seal around the female urethra and urethra of the male glans penis to reduce extra urethral contamination.

An even further object of the present invention is to provide a container which is easily sealable without allowing the bodily fluid specimen to be spilled, but which can be opened by laboratory personnel without difficulty.

Also an object of the present invention is to provide a device for taking urine samples which is simple, rapid and eliminates the need for transferring urine from a cup or bag to a centrifuge tube.

It is even a further object of the present invention to provide a system whereby a health care attendant or the patient can see when a centrifuge tube is filled and includes means to remove it before overflow occurs.

An even further object of the present invention is to provide an apparatus for use with a pediatric male to allow the device to be taped to the glans penis until a urine specimen is collected.

An even further object of the present invention is to reduce the health care workers exposure to urines which potentially house viral and bacterial infections.

A further object of the present invention is to provide a urine collection funnel capable of pushing the vaginal tissue around the urethral meatus away from the opening thereby decreasing contamination of the urine to be collected.

Another object of the present invention is to provide a container which is easy to hold and manage.

An even further object of the present invention is to decrease the health care workers exposure to seminal fluids.

More particularly, the present invention provides a device for collecting urine samples comprising:

an elongated flexible tubular conduit having a funnel-shaped first opening at one end and a second opening at the opposite end, said funnel-shaped opening being sized to fit around the outer periphery of a urethral meatus and to form a seal thereabout;

a sample collector having an opening therein; and, a plug disposed within said opening of said sample collector, said plug having means to receive said opposite end of said tubular conduit therethrough, said means to receive said opposite end of said tubular conduit including sealing means when not in receipt of said opposite end therein.

Even more particularly, the present invention provides a device for collecting body fluid samples comprising:

an elongated flexible tubular conduit having a funnel-shaped first opening at one end and a second opening at the opposite end;

a sample collector having an opening therein;

a closure member disposed within said opening of said sample collector, said closure member having means to receive said opposite end of said tubular conduit therethrough, said means to receive said opposite end of said tubular conduit including sealing means when not in receipt of said opposite end therein; and said closure member comprising a detachable stopper and a body with an opening extending longitudinally therethrough, said body receiving said stopper in said opening.

Accordingly, other objects, features and advantages of the present invention will be apparent by reference to the following description of preferred embodiments, drawings and claims.

BRIEF DESCRIPTION OF THE DRAWINGS

A better understanding of the present invention may be obtained from the following detailed description of the preferred embodiments described in connection with the accompanying drawings wherein.

DETAILED DESCRIPTION OF THE PREFERRED EMBODIMENTS

Figure 1:
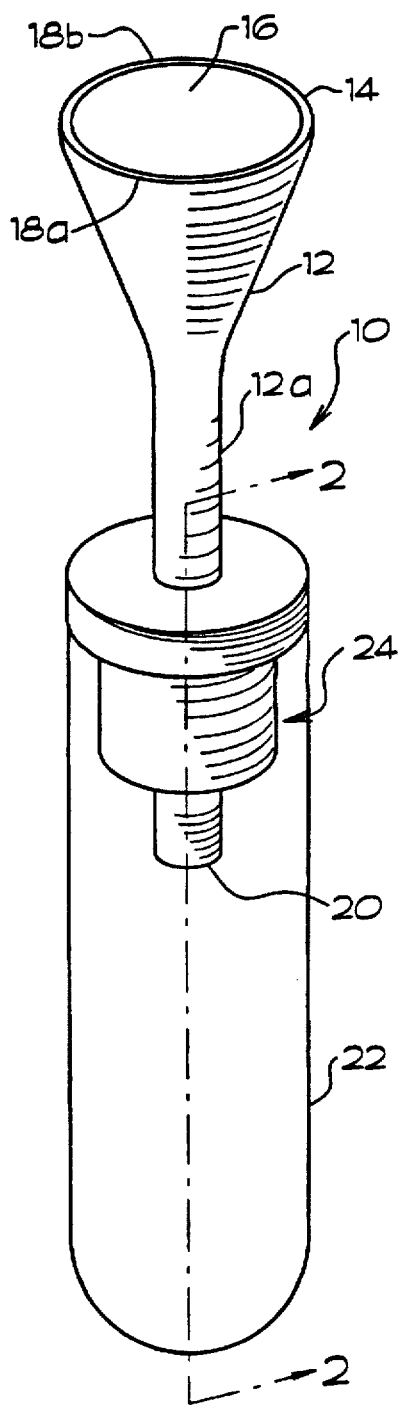
FIG. 1 is a perspective view of one preferred urine collection device of the present invention.

Referring now to the drawings, as best shown in FIG. 1, a body fluid sampling device 10, particularly for urine, comprises a flexible tubular conduit member 12, a closure 24 and a sample collector 22.

The flexible tubular conduit member 12 is provided with a funnel-shaped end 14 and a discharge end 20. Between the funnel-shaped end 14 and the discharge end 20 is a flexible tubular portion 12a.

Figure 6:
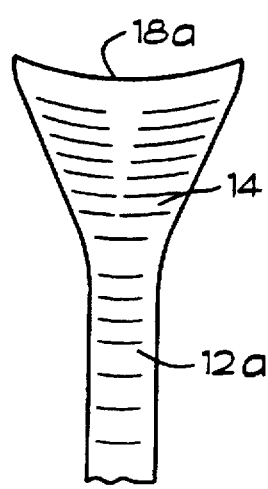
FIG. 6 is a side view of the funnel-shaped opening of the elongated flexible tubular conduit member shown in FIG. 1.
Figure 7:
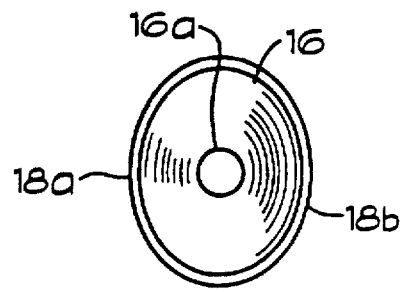
FIG. 7 is a top view of the funnel-shaped opening of the elongated flexible tubular conduit member shown in FIG. 1.

The funnel-shaped end 14 of the flexible tubular conduit member 12, as best shown in FIGS. 6 and 7, includes an elliptically-shaped opening 16 with concave-shaped sides 18a and 18b, and an opening 16a which provides means for the flow of fluid from the funnel-shaped end 14 into the flexible tubular portion 12a. However, it is realized that the opening 16 may be circular-shaped, and include fastening tabs 42 on each side thereof (FIG. 9) for attaching and holding the conduit member 12 onto the penis of a pediatric male.

Figure 2:
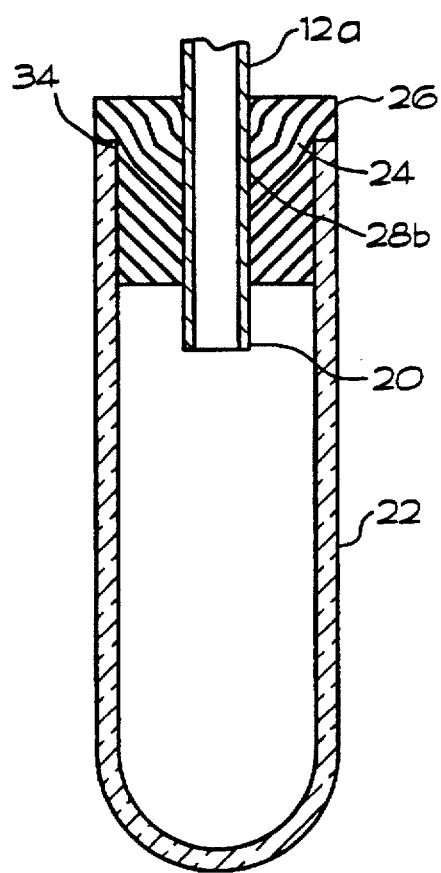
FIG. 2 is a cross-sectional view taken along line 2—2 of FIG. 1.

As best shown in FIG. 2, the sample collector 22 is provided with an opening 34 therein to receive the closure member 24.

The closure member 24, as shown in FIGS. 2, 3, 4 and 5 is cylindrically-shaped of T-shaped cross-section including a first cylindrical disc portion 26 unitary with a second cylindrical disc or valve portion 28 wherein said first disc 26 is of a greater diameter than said second disc 28. The first disc portion 26 covers the opening 34 in the sample collector 22. The cylindrically-shaped valve portion 28, which is generally made of a resilient elastomeric material, has an outer diameter substantially the same as the inner diameter of the opening 34 of the sample collector 22, so that upon insertion into the opening 34, the closure member 24 is in sealing relation with the sample collector 22 so the fluid collected within the sample collector 22 is maintained therein.

Figure 3:
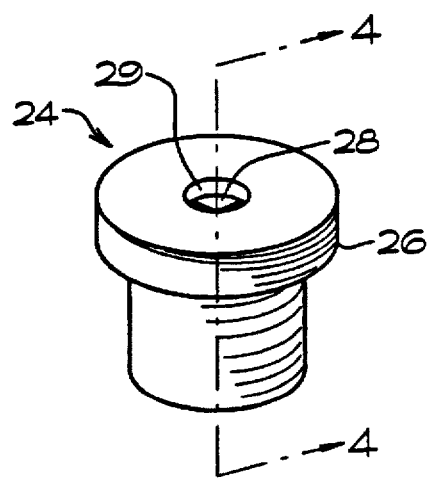
FIG. 3 is a perspective view of a closure member of the preferred embodiment as shown in FIG. 1.
Figure 4:
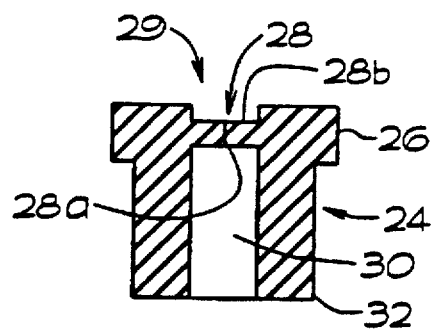
FIG. 4 is a cross-sectional view taken through line 4—4 of FIG. 3.
Figure 5:
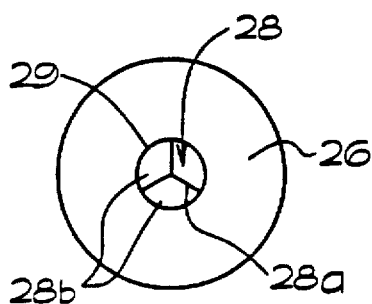
FIG. 5 is a top view of the closure member of FIG. 3.

As shown in FIGS. 3, 4 and 5, the closure member 24 also includes a centrally disposed opening 29 in the first disc portion 26 which is in flow communication with passageway 30 which is disposed centrally of the closure member 24. The opening 29 and the passageway 30 are in axial alignment and are sized with an inner diameter substantially the same as the outer diameter of the flexible tubular portion 12a of conduit member 12. The valve 28 is generally unitary with the first disc 26 and in one preferred embodiment includes three radial slits 28a which are equally spaced around the valve portion 28. And, the slits 28a extend completely between the opening 29 and the passageway 30.

Figure 8:
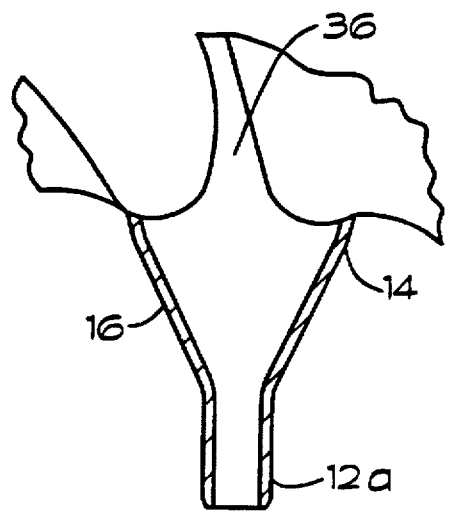
FIG. 8 is a cross-sectional view of the funnel-shaped end of the elongated conduit member of FIG. 1 in a use position with the urethra of a female and shows how the device is used to obtain urine samples.

As shown in FIG. 8, the funnel-shaped end 14, having an elliptically-shaped opening 16, is sized to fit over and in sealing relationship with the urethra 36 of an adult female.

Figure 9:
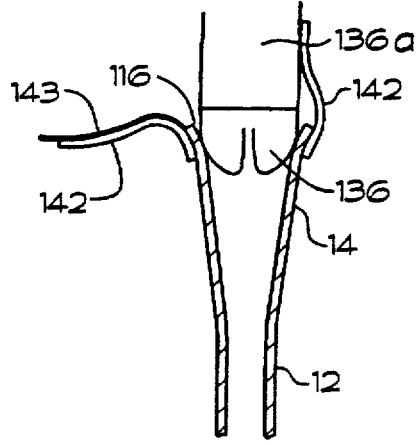
FIG. 9 is a cross-sectional view of another funnel-shaped end of an elongated conduit member of FIG. 1 in a use position with the glans penis of a pediatric male.

As shown in FIG. 9, the funnel-shaped end 14 is provided with a circularly-shaped opening 116 which is sized to fit the urethra of a glans penis 136 of an uncircumcised male and a pediatric male. For pediatric males, fastening tabs 142 are provided for attaching the end 14 to the glans penis 136 of the pediatric male. Fastening tabs 142 are shown as a pull back tape well known in the art having a backing 143 thereon. When attaching, backing 143 is pulled back and the tape portion 142 is attached to the shaft of the penis 136a and held thereon until a sample is received.

Figure 11:
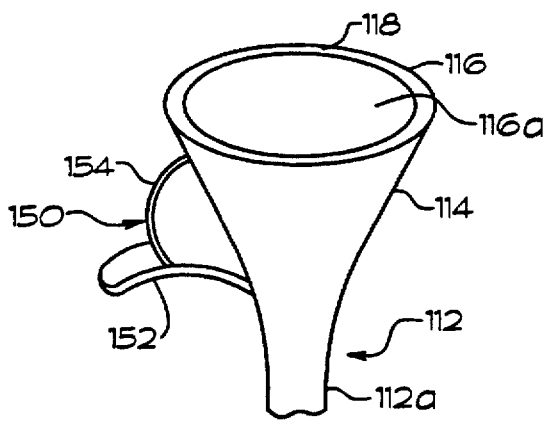
FIG. 11 is a perspective view of another preferred elongated flexible tubular conduit showing the funnel shaped first opening.
Figure 10:
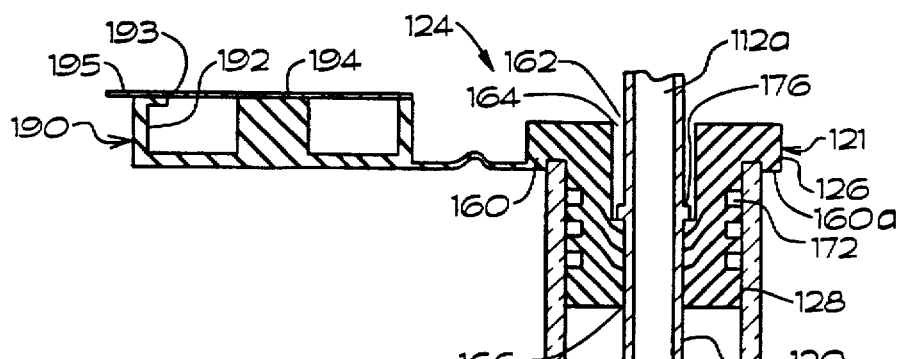
FIG. 10 is a cross-sectional view of another preferred closure member of the present invention.
Figure 10:
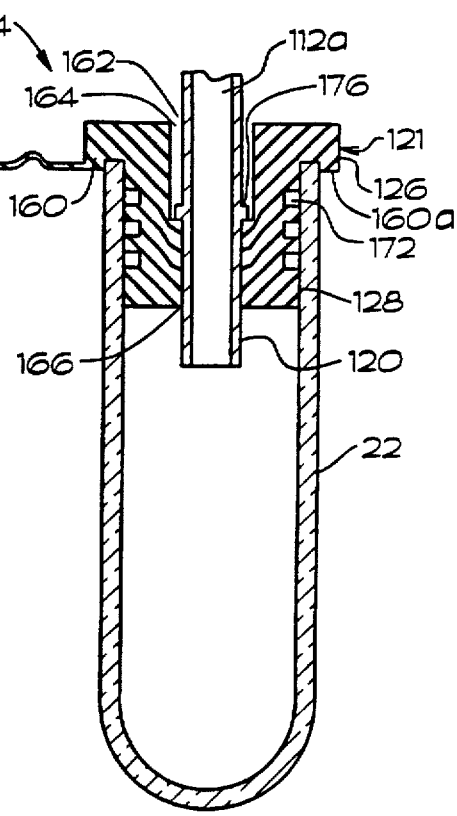

As best shown in FIGS. 10 and 11, another preferred body fluid sampling device, particularly useful for urine, is shown. The sampling device comprises a flexible tubular conduit member 112 (FIG. 11), a closure member 124, and the sample collector 22.

The flexible tubular conduit member 112 is provided with a funnel-shaped end 114 (FIG. 11) and a discharge end 120 (FIG. 10). Between the funnel-shaped end 114 and the discharge end 120 is a flexible tubular portion 112a. As best shown in FIG. 11, the funnel-shaped end 114 of the flexible tubular conduit member 112 includes an elliptically-shaped opening 116 with concave-shaped sides 118 and an opening 116a which provides for the flow of fluid from the funnel-shaped end 114 into the flexible tubular portion 112a. Preferably, concave-shaped sides 118 have rolled edges for better displacement of tissue on each side of the urethra. Also provided is a finger-engaging portion 150 which is provided for holding the funnel-shaped end 114 in contacting relationship with the urethra of a female or the glans penis of a male when in a use position. The finger-engaging portion 150 includes an outwardly extending semi-circular shaped portion 152 which extends outwardly from and is attached to the funnel-shaped end 114 of the elongated flexible tubular conduit 112. The curvature of the finger-engaging portion 152 is shaped to fit against an adult finger. Also provided is a support 154 for the finger engaging portion 152, the support 154 being attached to the convex or upper surface of the semi-circular shaped portion 152 and along the funnel-shaped end 114 of the flexible tubular conduit member 112. The function of the support member 154 is to provide rigidity to the finger engaging portion 152.

The closure member 124, as shown in FIG. 10, includes a body 121 and a stopper 190. Body 121 is generally cylindrically shaped of T-shaped cross-section including an outer cylindrical disc portion 126 and unitary therewith, an inner cylindrical disc portion 128. The outer cylindrical disc 126 is provided with flanged portion 160 which extends around the outer periphery of the disc 126. The flange 160 is parallel to and extends in the same direction as the inner disc portion 128. Flange 160 is spaced from the outer periphery of the inner disc 128, the distance between the outer periphery of the disc portion 128 and the inner periphery of the flange 160 being approximately the thickness of the walls of the sample collector 22 so that the body portion 121 fits in sealing relationship with the open end of the sample collector 22.

Figure 12:
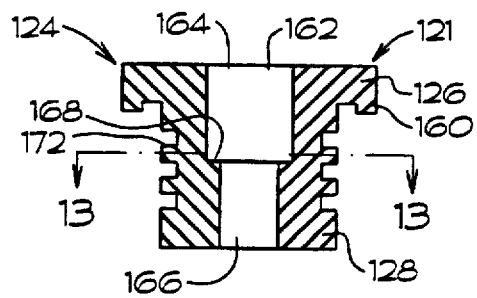
FIG. 12 is a cross-sectional view of a closure member shown in FIG. 10 with the elongated flexible tubular conduit removed.

As best shown in FIG. 12, the body portion 121 includes an opening 162 therethrough. The opening 162 has a diameter at an inlet end 164 greater than the diameter at an outlet end 166. As shown in FIG. 12, the opening 162 is provided with parallel sides with step 168 at the juncture of the inlet end 164 with the outlet end 166. Step 168 separates the inlet end 164 from the outlet end 166. However, it is realized that the opening 162 may also be tapered as shown in FIG. 10, wherein the opening 162 tapers inwardly from the inlet end 164 to the outlet end 166.

Also provided along the walls of the opening 162 at the outlet end 166 is a plurality of air ventilating channels 170 (FIG. 13) which extend from the step 168 to the terminating end of the outlet end 166.

As shown in FIGS. 10 and 12, the body portion 121 of the closure member 124 includes a plurality of grooves 172 which extend along the outer periphery of the inner disc 128. The grooves 172 are provided to allow for ease of operation in inserting and removing the body member 121 from the sample collector 22 but also to provide a seal between the inner disc 128 and the inner walls of the sample collector 22.

As shown in FIG. 10, the flexible tubular conduit member 112 adjacent to its discharge end 120 includes at least one circumscribing ridge 176 which is received within the opening 162 in a use position. The outer diameter of the ridge 176 is slightly greater than the diameter of the outlet end 166, but the radius of the ridge 176 is less than the distance from the center of the outlet end 166 to the outer extremities of air ventilating channels 170. Ridge 176 provides a stop for the insertion of tubular member 112 into opening 162 as well as efficient and easy means for insertion and removal of tubular member 112 into and out of the opening 162 as the outer diameter of the flexible tubular conduit member 112 is generally substantially the same as or slightly greater than the opening 162 at its exit end 166. Stop or ridge 176 provides a seal over the opening into the sample collector 22, but does not cover the air ventilation channels 170.

As also shown in FIG. 10, the closure member 124 includes a detachable stopper 190 of E-shaped configuration in cross-section. The stopper 190 includes an outer flange portion 192 which extends circumferentially around the outer extremity of the stopper 190 and a centrally disposed inner disc portion 194. The inner disc portion 194 is of substantially the same shape and cross-sectional area as the inlet end 164 of the body portion 121. The distance between the outer extremity of the disc 194 and the inner extremity of the flange 192 is substantially the same as the distance between the outer perimeter of the opening 162 at the inlet end 164 and the outer extremity of the disc portion 126. In a non-use position or after a fluid sample has been collected, the detachable stopper 190 can be placed over the body portion 121 to seal the collected fluid therein for transporting to a centrifuge or other processing equipment.

Detachable stopper 190 further includes a snap lock 193 which is an inwardly protruding lip portion at the outer extremity of outwardly extending flange 192. Snap lock 193 locks stopper 190 to body member 121 by engaging with an underneath portion 160a of flange 160. Also provided is a sealed covering 195 over the detachable stopper 190. Sealed covering 195 is generally a flexible material, such as a thin plastic, wax paper, or the like, which provides for a sterile covering of the stopper 190 prior to use in capping or plugging the body 121 of closure member 124.

Figure 13:
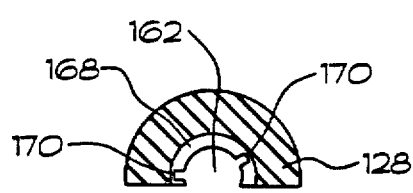
FIG. 13 is a cross-sectional view taken along line 13—13 of FIG. 12.
Figure 14:
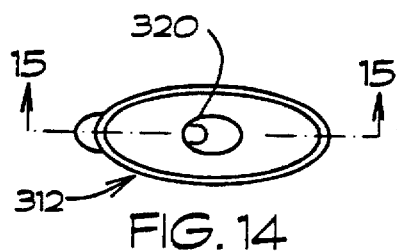
FIG. 14 is a top view of the flexible tubular conduit of FIG. 11.
Figure 16:
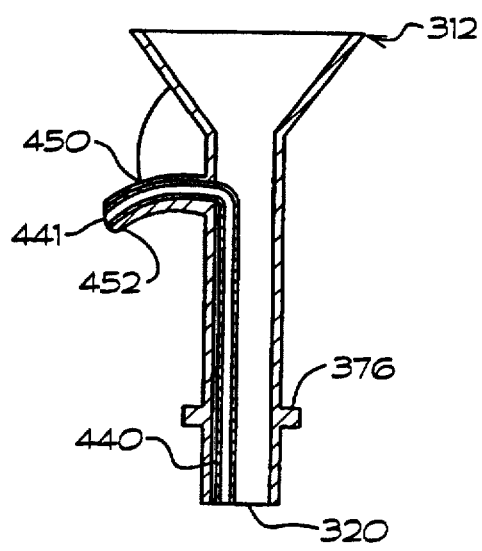
FIG. 16 is a cross-sectional view taken along line 15—15 of FIG. 14 of an alternate preferred flexible tubular conduit of the present invention.
Figure 15:
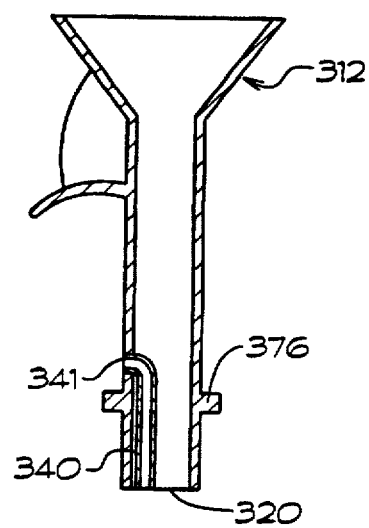
FIG. 15 is a cross-sectional view taken along line 15—15 of FIG. 14.

As shown in FIGS. 14, 15 and 16, means for venting air from the sample collector 22 may include vent air conduits 340 (FIG. 15), 440 (FIG. 16) which extend from the exit end 320 of flexible tubular conduit member 312 upwards to the position above a tubular circumscribing ridge 376 which fits over the opening in a closure member, such as opening 162 in closure member 124 in FIG. 13. As shown in FIG. 15, vent air conduit 340 has an outlet opening 341 just above ridge 376 and in FIG. 16, vent air conduit 440 has an outlet opening 441 co-extensive with the semi-circular shaped portion 452 of a finger engaging portion 450.

Figure 17:
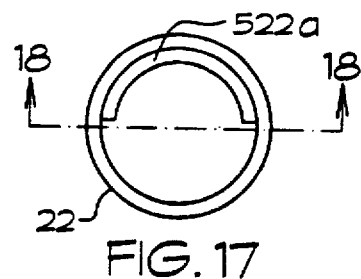
FIG. 17 is a top view of a sample collector of the present invention.
Figure 18:
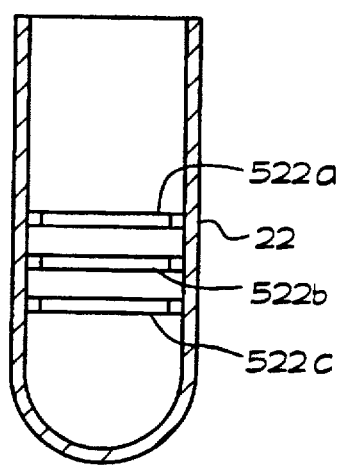
FIG. 18 is a cross-sectional view taken along line 18—18 of FIG. 17.

As shown in FIGS. 17 and 18, the sample collector 22 may be provided with means to analyze selected chemicals in a fluid specimen substantially simultaneously with the taking of the fluid sample. One means is to attach preselected test strips 522a, 522b and 522c around the inner circumference or periphery of the collector 22. It is realized that more or less than three test strips 522a, 522b and 522c may be utilized. Also it is realized that test strips may also be allowed to float freely within the fluid sample.

Figure 19:
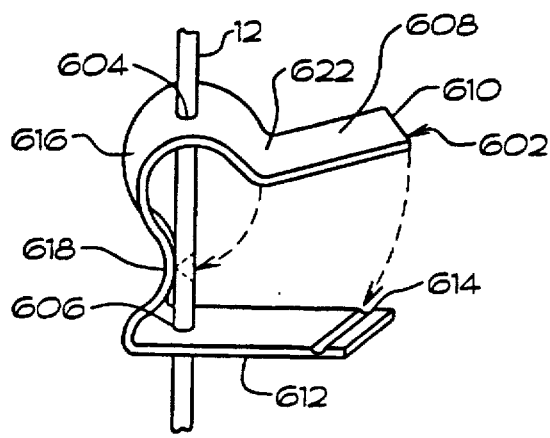
FIG. 19 is a perspective view of a tubular conduit member of the present invention with a spring-lock device for cutting off the flow of fluids therethrough.

A means to cut off the flow of fluid into a sample collector 22 through flexible tubular conduit 12 may also be utilized. Many different types of valve means may be used, but one preferred means to cut off the flow of fluid into a sample collector 22 is shown in FIG. 19. In FIG. 19, a spring latch device 602 is provided to cut off the flow of fluid through tubular conduit 12 when a desired amount of specimen has been received in sample collector 22. Spring latch device 602 is provided with a pair of spaced openings 604, 606 to receive tubular conduit 12 therethrough. Spring latch 602 is provided with an outwardly extending latch portion 608 having a tip 610 at its extreme end and an outwardly extending latch receiving portion 612 having a notch 614 therein to receive tip 610 in a latching position. Connecting latch portion 608 to latch receiving portion 612 is a serpentine section 616 having a mid-section 618 for engaging with tubular conduit 12. At the connection of latch portion 608 to serpentine section 616 is a generally V-shaped juncture 622 which is positioned to engage mid section 618 with tubular conduit 12 squeezed or closed therebetween when the tip 610 is received within notch 614, as illustrated by dotted lines.

In operation, the sample collector 22 which is usually a centrifuge tube, is provided with a closure member 24, 124 disposed in sealing relationship with the interior thereof. The funnel-shaped end 14, 114 of the flexible tubular conduit member is then positioned as shown in FIG. 8 over the urethra 36 of an adult female or in FIG. 9 over the glans penis 136 of a male and the discharge end 20, 120 of the flexible tubular conduit 12 is inserted within the closure member 24, 124. The end 20, 120 is pushed through the valve or disc portion 28, 128 wherein the slits 28a or opening 162 yield to the discharge end 20, 120 passing therethrough. The fluid specimen is then deposited into the centrifuge tube and upon completion of the collection of the fluid specimen, the discharge end 20, 120 of the flexible tubular conduit member 12, 112 is then removed from the closure member 24, 124. The sample collector 22 is then sealed by the return of the valve portion 28 to its closed position or by detachable stopper 190 and the centrifuge tube or sample collector 22 is then taken away for analysis.

It is realized that other variations and modifications of the preferred embodiment are possible without departing from the scope and spirit of the present invention. And, it is not intended that the aforementioned discussion in any way limits the scope of the present invention as set forth in the appended claims.

What is claimed is:

1. A device for collecting urine samples comprising:
   an elongated flexible tubular conduit having a funnel-shaped first opening at one end and a second opening at the opposite end, said conduit having holding means adjacent said funnel-shaped first opening, said holding means being positioned to hold said funnel-shaped first opening in contacting relationship with a urethra when in a use position;
   a sample collector having an opening therein;
   a closure member disposed within said opening of said sample collector, said closure member having means to receive said opposite end of said tubular conduit therethrough, said means to receive said opposite end of said tubular conduit including sealing means when not in receipt of said opposite end therein; and,
   said closure member comprising a detachable stopper and a body with an opening extending longitudinally therethrough, said body receiving said stopper in said opening, said body having air vents means therein.

2. The device of claim 1, said air vent means including at least one air passage extending longitudinally along an inner periphery of said body, said inner periphery defining said opening.

3. The device of claim 2, said air vent means extends along an outlet end of said opening a preselected distance therealong.

4. The device of claim 3, said preselected distance being sufficient to provide means for air to vent from said sample collector during use.

5. The device of claim 1, said stopper comprising a cap portion with an outer flange and an inner disc, said outer flange configured to fit over an outer periphery of said body and said inner disc configured to fit within said opening.

6. The device of claim 1, said body including at least one circumscribing groove around the outer periphery.

7. The device of claim 1, said tubular conduit having at least one ridge circumscribing an outer periphery of said conduit, said ridge being spaced a preselected distance from said opposite end.

8. The device of claim 7, said ridge having an outer diameter slightly less than said diameter of said inlet end and greater than said outlet end.

9. The device of claim 1, said opening in said body having an inlet end and an outlet end, said inlet end having a greater diameter than said outlet end, said outlet end diameter being substantially the same or slightly less than the outer periphery of said opposite end of said conduit.

10. The device of claim 9, the diameter of said opening tapering inwardly from said inlet end to said outlet end.

11. The device of claim 1 wherein said funnel-shaped opening is sized to fit around the outer periphery of a urethra and to form a seal thereabout.

12. The device of claim 1 including valve means to cut-off flow through said flexible tubular conduit.

13. The device of claim 12, said valve means being a spring latch device, said spring latch device including means to receive said tubular conduit therethrough and means to close-off flow through said tubular conduit in a latching position.

14. The device of claim 1, said sample collector including sample test means therein.

15. The device of claim 14, said sample test means including at least one sample test strip circumscribing a selected portion of an inner periphery of said sample collector.

16. The device of claim 1, said funnel-shaped opening having concave-shaped sides.

17. The device of claim 16, said sides having rolled edges.

* * * * *